(12) United States Patent
Hwang et al.

(10) Patent No.: US 10,078,069 B2
(45) Date of Patent: Sep. 18, 2018

(54) DEVICE FOR DETECTING CHANGE IN UNDERGROUND MEDIUM

(71) Applicant: ELECTRONICS AND TELECOMMUNICATIONS RESEARCH INSTITUTE, Daejeon (KR)

(72) Inventors: Gunn Hwang, Daejeon (KR); Sung Q Lee, Daejeon (KR); WooSub Youm, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 358 days.

(21) Appl. No.: 14/949,628

(22) Filed: Nov. 23, 2015

(65) Prior Publication Data

US 2016/0146760 A1     May 26, 2016

(30) Foreign Application Priority Data

Nov. 24, 2014  (KR) .................. 10-2014-0164537
Oct. 21, 2015   (KR) .................. 10-2015-0146829

(51) Int. Cl.
| | | |
|---|---|---|
| G01N 29/02 | (2006.01) | |
| E21B 47/10 | (2012.01) | |
| G01N 29/024 | (2006.01) | |
| G01M 3/24 | (2006.01) | |
| G01N 29/07 | (2006.01) | |
| F17D 5/06 | (2006.01) | |

(52) U.S. Cl.
CPC ......... *G01N 29/024* (2013.01); *E21B 47/101* (2013.01); *E21B 47/102* (2013.01); *F17D 5/06* (2013.01); *G01M 3/24* (2013.01); *G01N 29/07* (2013.01); *F16L 2201/30* (2013.01); *G01N 2291/011* (2013.01)

(58) Field of Classification Search
None
See application file for complete search history.

(56) References Cited

U.S. PATENT DOCUMENTS 4,077,253 A *  3/1978  Grisell ................ A61B 8/08
                                                    367/7
4,751,689 A    6/1988  Kobayashi
(Continued)

OTHER PUBLICATIONS

T. Hao et al., "Condition assessment of the buried utility service infrastructure", Tunnelling and Underground Space Technology, 2012, pp. 331-344, vol. 28, Elsevier Ltd.

*Primary Examiner* — Harshad R Patel

(57) ABSTRACT

The inventive concept relates to a device that detects a leak of a liquid leaked from a sinkhole, water pipe or oil pipeline under the ground. In the detection device of the inventive concept, a plurality of reception devices disposed on the surface of the earth simultaneously receive an ultrasonic signal transmitted from a transmission device under the ground and a radio frequency (RF) signal synchronized with the ultrasonic signal. Also, by measuring an arrival time of the ultrasonic signal by using the wireless signal received by each reception device as a triggering signal, a leak range of a liquid leaked from a sinkhole, water pipe or oil pipeline on a signal path between the transmission device and the reception device is detected.

14 Claims, 3 Drawing Sheets

(56) References Cited

U.S. PATENT DOCUMENTS

| | | | | |
|---|---|---|---|---|
| 4,813,025 A | * | 3/1989 | Rowland | G01S 15/74 128/201.19 |
| 6,442,999 B1 | * | 9/2002 | Baumoel | G01F 1/66 73/40.5 A |
| 2003/0142587 A1 | * | 7/2003 | Zeitzew | G01S 7/52004 367/127 |
| 2008/0047329 A1 | * | 2/2008 | Breed | G01N 35/00871 73/61.41 |
| 2009/0153307 A1 | | 6/2009 | Kim et al. | |
| 2009/0262604 A1 | | 10/2009 | Funada | |
| 2010/0286949 A1 | * | 11/2010 | Miyamoto | G01S 5/30 367/127 |
| 2011/0116345 A1 | * | 5/2011 | Miyamoto | G06F 3/03545 367/124 |
| 2011/0148419 A1 | | 6/2011 | Cho et al. | |
| 2011/0261654 A1 | * | 10/2011 | Miyamoto | G01S 5/18 367/125 |
| 2014/0112104 A1 | | 4/2014 | Calvarese | |

* cited by examiner

DEVICE FOR DETECTING CHANGE IN UNDERGROUND MEDIUM

CROSS-REFERENCE TO RELATED APPLICATIONS

This U.S. non-provisional patent application claims priority under 35 U.S.C. § 119 of Korean Patent Application Nos. 10-2014-0164537, filed on Nov. 24, 2014, and 10-2015-0146829, filed on Oct. 21, 2015, the entire contents of which are hereby incorporated by reference.

BACKGROUND

The present disclosure herein relates to a detection system, and more particularly to, a device for detecting a change in an underground medium using an arrival time of an ultrasonic signal.

A patent related to a method of measuring a position by using a difference in transmission time is disclosed in U.S. Patent Publication No. US 2014/00112104 A1 (ULTRASONIC LOCATION USING ONLY TIME DIFFERENCE OF ARRIVAL MEASUREMENTS). The above invention discloses a method of measuring a position by using a transmission delay time of an ultrasonic signal.

Also, a research topic on the water leak measurement of an underground conduit has been studied. T. Hao (Condition assessment of the buried utility service infrastructure, Tunneling and Underground Space Technology 28 (2012) 331-344) discloses a study on methods of finding water leak in various conduits.

However, the above patent and features mostly have the concept of a method of calculating a position according to an ultrasonic signal delay time but do not disclose a method of calculating the distribution range of an underground medium by utilizing an electromagnetic wave and ultrasonic signal.

SUMMARY

The present disclosure provides a device and method for detecting a change in underground medium that detects the distribution range of a liquid, namely, the thickness and width of a liquid that is underground by the leak of a liquid leaked from an underground cavity, water pipe or oil pipeline.

An embodiment of the inventive concept provides an underground medium detection device in which that a plurality of reception devices on the surface of the earth simultaneously receives an ultrasonic signal transmitted by a transmission device under the ground and a radio frequency (RF) signal synchronized with the ultrasonic signal, and a delay time between two signals received by each reception device is measured to find the distribution range of an underground medium, such as the leak range of a liquid leaked from a cavity, water pipe or oil pipeline on a signal path between the reception device and the transmission device based on the measured delay time.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
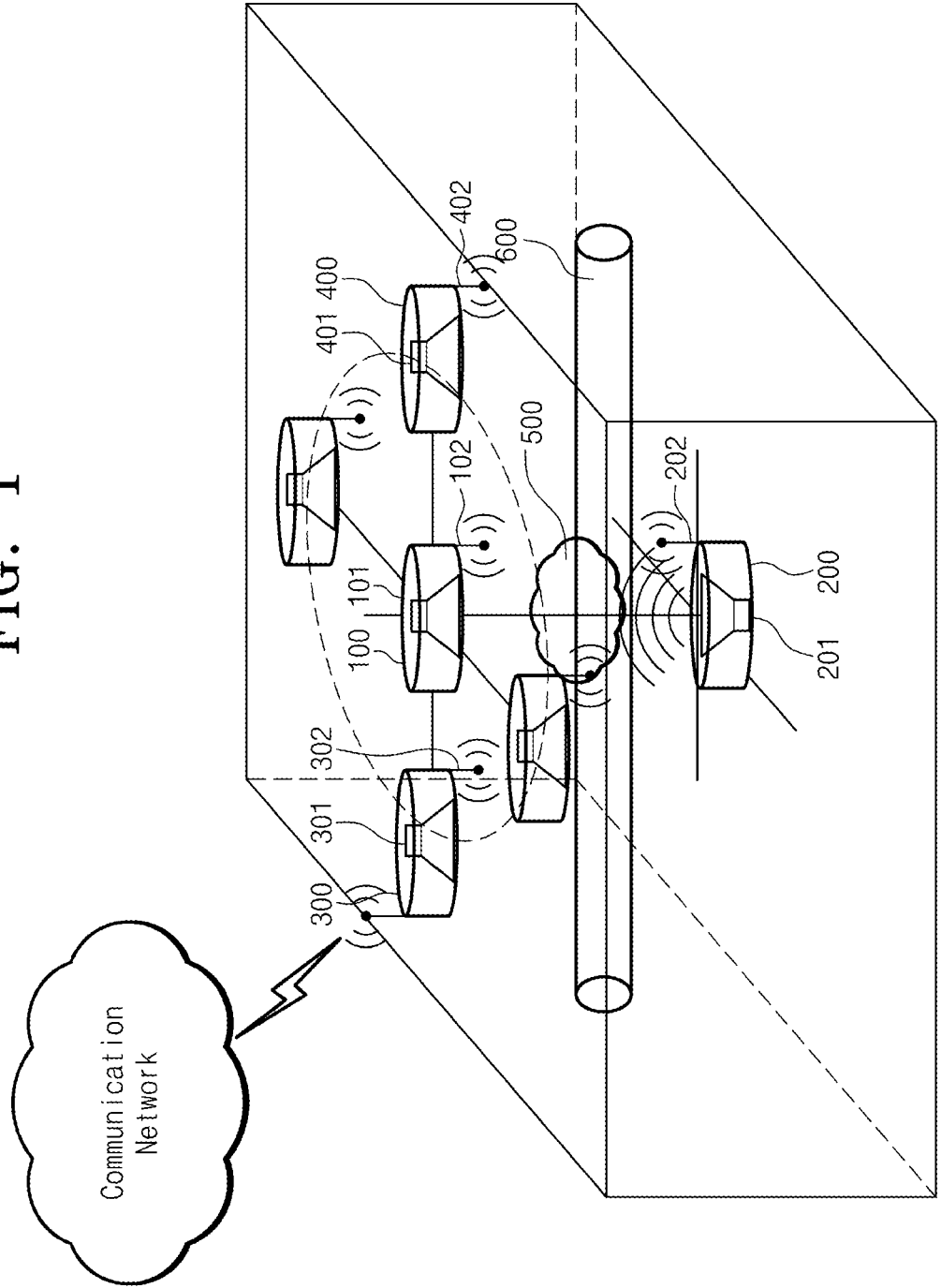
FIG. 1 illustrates an ultrasonic application water leak detection device according to an embodiment of the inventive concept.

In the following, embodiments according to the inventive concept are described in detail with reference to the accompanying drawings. It should be noted that in the following descriptions, only parts required for understanding operations according to the inventive concept are described, and the descriptions of other parts are omitted in order not to obscure the subject matter of the inventive concept.

The inventive concept relates to a method of receiving a synchronized ultrasonic signal and a radio frequency (RF) signal by a plurality of reception devices on the surface of the earth when a transmission device under the ground transmits them, and measuring an arrival time of the received ultrasonic signal by using a wireless signal received by each reception device as a triggering signal to detect the leak of a liquid leaked from a cavity, water pipe or oil pipeline at a signal path between the reception device and the transmission device based on the measured arrival time.

The inventive concept is characterized in that a transmission device under the ground transmits an ultrasonic signal and an RF signal synchronized therewith simultaneously and a reception device receives the two signals so that the size of a liquid or space on a signal path is calculated by utilizing a difference in delay time between two signals, and such a method has advantages in that it is possible to remove a cable part between the transmission device and the reception device because of a structural characteristic, thus it is easy to install, a structure is also simple, the structures of the transmission and reception devices are also simplified and it is possible to manufacture at a low cost. Also, since the inventive concept does not detect the presence and absence of a liquid unlike a typical water sensor and uses a physical phenomenon in which an ultrasonic speed varies depending on a medium, such as a liquid, solid, gas, etc., there is an advantage in that it is possible to be aware of the distribution of an underground medium in addition to simple distance information.

The inventive concept is to implement a method for detecting the distribution range of a liquid, namely, the thickness and width of a liquid that is underground by the leak of a liquid leaked from an underground cavity, water pipe or oil pipeline. To this end, an underground medium detection device includes a transmission device under the ground and a reception device over the ground. The underground transmission device includes an ultrasonic transceiver, a circuit unit related to wireless communication and ultrasonic transmission and reception, and a power supply unit that includes a secondary battery to supply power. The reception device over the surface of the earth includes an ultrasonic transceiver, a circuit unit related to wireless communication and ultrasonic transmission and reception, and a power supply unit that includes a secondary battery to supply power and power may also be directly supplied by using a cable.

An ultrasonic application device according to the inventive concept is characterized by a method of receiving an ultrasonic signal transmitted by a transmission device under the ground and an RF signal synchronized with the ultrasonic signal simultaneously by a plurality of reception devices on the surface of the earth, and measuring a delay time between two signals received by each reception device to find the distribution range of an underground medium, such as the leak range of a liquid leaked from a cavity, water pipe or oil pipeline on a signal path between the reception device and the transmission device based on the measured delay time.

Through the inventive concept, it is possible to manufacture an ultrasonic transmission and reception system of an integrated module structure in which an ultrasonic transmission and reception unit, a wireless circuit unit, and a battery unit that may measure an underground cavity or water leak by using a signal delay between a synchronized ultrasonic signal and an RF signal, thus it is also possible to detect water leak remotely in real time when there is a connection to a sensor network. Also, a typical water leak detection device may malfunction because it is difficult to detect an amount of leak when it rains or even when there is little water leak, but the inventive concept has high reliability because a water leak range due to a water leak is measured. Also, since there is a need to bury only a transmission device, it is cheap, it is easy to install and it is possible to reduce an installation cost. Since it is also possible to detect the generation of a cavity when data is continuously observed, there is an effect in that it is possible to prevent a disaster according to the generation of the cavity.

The propagation speed of a sound wave is 330 m/s in the air, 1450 m/s in the water, and 5000 m/s in granite. When the sound speed and time of flight (TOF) of these mediums are found, it is possible to find a distance between two positions. In this case, the transmission speed of an electromagnetic signal is the same as the speed of light and constant irrespective of the medium, but the transmission speed of an ultrasonic signal varies depending on a medium on a signal path. A method of finding such a transmission speed may apply a threshold detection technique, an envelope estimation technique, a frequency recognition technique, and a phase shift technique.

FIG. 1 illustrates an ultrasonic application water leak detection device according to an embodiment of the inventive concept.

Referring to FIG. 1, the ultrasonic application water leak detection device may include an ultrasonic/wireless transmission device 200 and an ultrasonic/wireless reception device 100, for example.

The ultrasonic/wireless reception device 100 may be located at the surface of the earth. The ultrasonic/wireless reception device 100 may include an ultrasonic reception unit 101 and a wireless transmission and reception unit 102.

The ultrasonic/wireless transmission device 200 is installed at an underground target, e.g., under a water pipe 600. The ultrasonic/wireless transmission device 200 may include an ultrasonic transmission unit 201 and a wireless transmission and reception unit 202.

For the convenience of understanding, a leaked liquid 500 is shown between the connections of the water pipe 600.

The ultrasonic/wireless transmission device 200 is located under the water pipe 600 to transmit an ultrasonic signal and an RF signal to the surface of the earth.

At least one ultrasonic/wireless reception device 100 is disposed at the surface of the earth, and receives the ultrasonic signal and the RF signal that are transmitted by the ultrasonic/wireless transmission device 200.

The RF signal is used as a triggering signal by the ultrasonic/wireless reception device 100. The ultrasonic/wireless reception device 100 detects the size of an underground soil component on a reception path of the ultrasonic signal based on the size of sound speed that varies depending on the component of a medium on the reception path by measuring the arrival time of the ultrasonic signal. Eventually, in FIG. 1, the size of water leak is detected.

Since a plurality of the ultrasonic/wireless reception device 100 is disposed at certain intervals at the surface of the earth, the size of the underground soil component may be 3-dimensionally detected. The ultrasonic/wireless transmission device 200 may have a structure in which power is provided from a primary battery and thus there is no need for an external power supply, a structure in which power is received through a power cable extended from the surface of the earth, or a structure in which a secondary battery is included and charging is performed wirelessly through a magnetic field or ultrasonic wave provided from the surface of the earth.

Similarly, the ultrasonic/wireless reception device 100 may also have a structure in which power is provided from a primary battery and thus there is no need for an external power supply, a structure in which power is received through a power cable extended from a power supply device at the surface of the earth, or a structure in which a secondary battery is included and charging is performed wirelessly through a magnetic field or ultrasonic wave provided from a power supply device at the surface of the earth.

The ultrasonic/wireless reception devices 100 may communicate within reception devices and one of them may be configured so that it is connected to an external communication network through a sensor gateway to be capable of obtaining operation and measurement data on a transmission and reception device remotely.

The ultrasonic/wireless reception device 100 may be configured to communicate with the ultrasonic/wireless transmission device 200 wirelessly or by using an ultrasonic wave and change the ultrasonic/wireless transmission device to a sleep mode or operating mode remotely.

The ultrasonic/wireless reception device 100 and the ultrasonic/wireless transmission device 200 may be configured to be automatically changed to the sleep mode for power saving when it is in a non-operating mode for a certain time.

When there is one or more ultrasonic/wireless transmission device 200, there may be also one or more ultrasonic/wireless reception device 100 so that they may be combined each other in order to detect a change in underground target medium. Also, when there is one ore more ultrasonic/wireless transmission device 200, the frequencies of transmission signals are different from each other to be capable of identifying a generation device or the number of a transmission device is transmitted through the header part of a signal so that a reception device may identify.

The ultrasonic signal is a signal of a pulse wave form or sine wave form and the measurement of the arrival time may be obtained by using a difference between the pulses of the ultrasonic signal and the RF signal or a difference between phases.

The ultrasonic/wireless reception devices 100 may be disposed in plurality on a concentric circle in a radial direction or may be disposed in plurality in a polygon including a quadrilateral such as a checker board.

The arrival time of an ultrasonic signal measured immediately after the ultrasonic/wireless transmission device 200 and the ultrasonic/wireless reception device 100 are installed is set as a criterion, and the arrival time of the ultrasonic signal measured after a certain time is compared with the set criterion so that a change in underground target medium on a signal path may be detected.

By measuring a speed difference relative to a change in underground medium after calculating an ultrasonic speed in the medium of the underground target through mathematical modeling, it is possible to detect the water leak, a sinkhole (cavity) or pollution of the underground target.

The RF signal may increase or decrease in frequency according to an attenuation level on the surface of the earth, and may be a signal of a pulse wave form or sine wave form.

Figure 2:
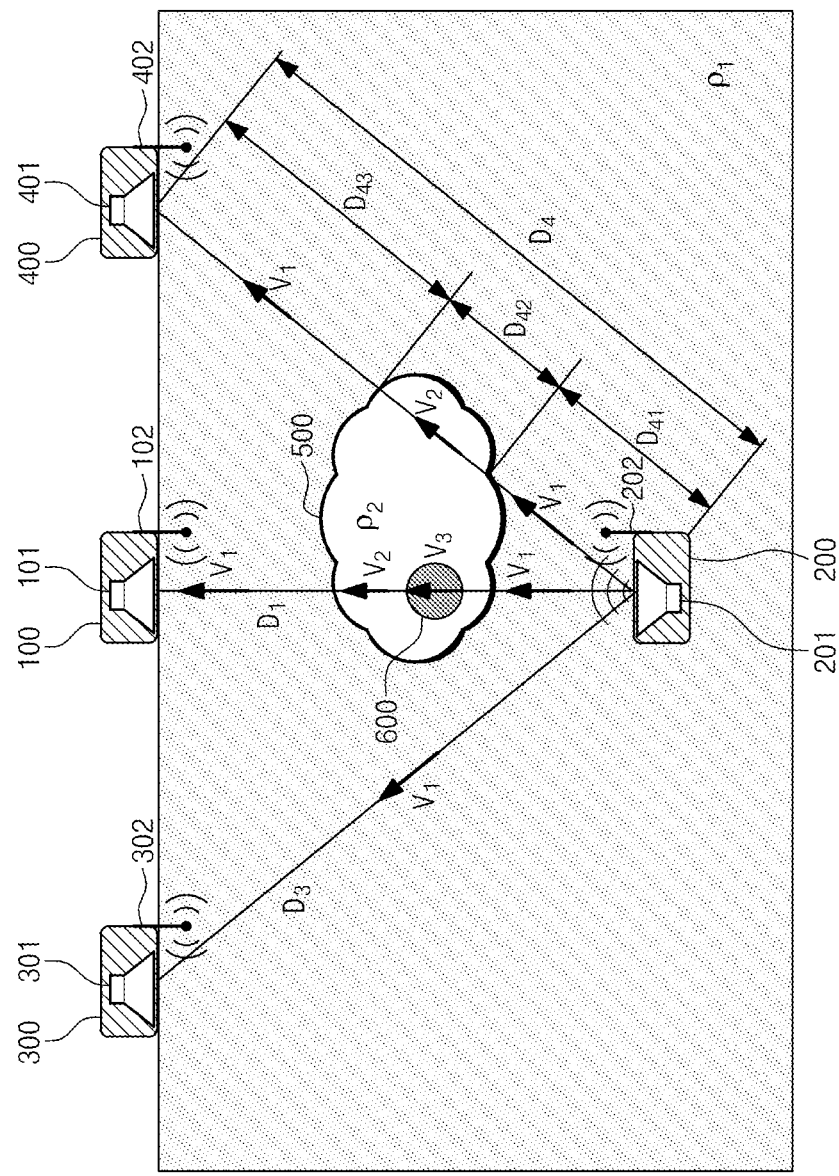
FIG. 2 illustrates a change in speed according to a medium in an ultrasonic application water leak detection device according to an embodiment of the inventive concept.
Figure 3:
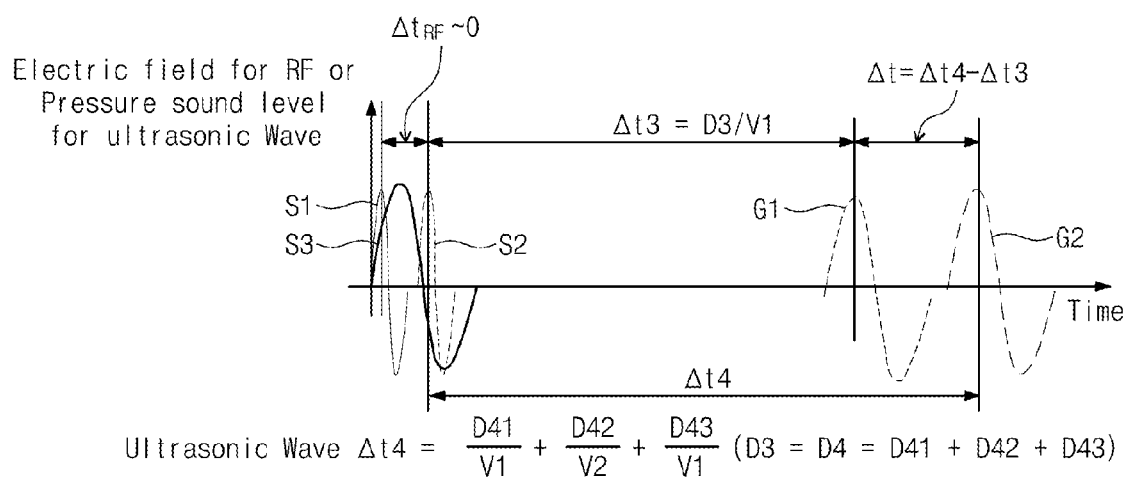
FIG. 3 is an exemplary signal waveform diagram according to FIG. 2.

FIG. 2 illustrates a change in speed according to a medium in an ultrasonic application water leak detection device according to an embodiment of the inventive concept. FIG. 3 is an exemplary signal waveform diagram according to FIG. 2.

Referring to FIG. 2, an example (cross-sectional view) of a configuration of the ultrasonic application water leak shows that there is the water pipe 600 between the ultrasonic/wireless transmission device 200 and the ultrasonic/wireless reception device 100 and there is a leaked liquid 500 around the water pipe 600. When the ultrasonic/wireless transmission device 200 transmits a synchronized ultrasonic signal and an RF signal as in FIG. 3, these signals are transmitted to the ultrasonic/wireless reception devices 100, 300 and 400 along the paths D1, D3 and D4, respectively.

When it is assumed that in soil having medium density of $\rho_1$, the propagation speed and transmission time of an ultrasonic wave are V1 and TOF1 respectively, and in the same medium, the speed and transmission time of an RF signal are V2 and TOF2 respectively a total delay time of $\Delta T$ in a distance D may be found by Equation (1) below:

$$\Delta T = TOF_1 - TOF_2 \qquad (1).$$

S1 in the signal waveform of FIG. 3 represents an RF signal, S3 represents an ultrasonic signal synchronized with the RF signal, S2 represents an RF signal transmitted through a transmission path, and G1 represents an ultrasonic signal when there is no other medium, namely, when there is no water leak, no oil leak or no sinkhole. G2 represents a delayed ultrasonic signal when there is another medium, namely, when there is a water leak, oil leak or sinkhole.

When a medium is constant on a signal path as in D3, a signal delay time $\Delta T_3$ may be found by Equation (2) below:

$$\Delta T_3 = \frac{D_3}{V_1}. \qquad (2)$$

When after installation of the device of the inventive concept, there is a space between the ultrasonic/wireless transmission device 200 and the ultrasonic/wireless reception device 100 for many reasons and thus there is a cavity, or there is water due to the water leak of a water pipe and thus there is a path such as D4, the signal delay time $\Delta T_4$ is found by Equation (3) below:

$$\Delta T_4 = \Delta T_{41} + \Delta T_{42} + \Delta T_{43} = \frac{D_{41}}{V_1} + \frac{D_{42}}{V_2} + \frac{D_{43}}{V_1} \qquad (3)$$

where D4=D3=D41+D42+D43 when D3 and D4 are the same distance and the same path, they mean paths in which mediums vary over time.

When the ultrasonic signal propagation time between the ultrasonic/wireless transmission device 200 and the ultrasonic/wireless reception device 100 is delayed from $\Delta T_3$ to $\Delta T_4$ on the same path, it may be aware that there is a change in speed according to a change in medium corresponding to the delay time. As such, it is possible to detect a change in medium by using a change in the ultrasonic signal delay time between the ultrasonic/wireless transmission device 200 and the ultrasonic/wireless reception device 100. The time difference between the time delay $\Delta T_3$ when there is no cavity and the time delay $\Delta T_4$ when there is a cavity determines the size of a cavity.

The ultrasonic signal delay time may be found by using the time difference but may also be found by using a phase difference appearing when a periodic wave, such as a sine wave is used and a person skilled in the art may easily implement it.

The underground medium change detection device of the inventive concept may manufacture an ultrasonic transmission and reception device of an integrated module structure in which an ultrasonic transmission and reception unit, a wireless circuit unit, and a power supply unit that may measure an underground cavity or water leak by using a signal delay between an ultrasonic signal and an RF signal, thus it is also possible to detect a water leak remotely in real time when there is a connection to a sensor network. Also, a typical water leak detection device may malfunction because it is difficult to detect an amount of leak when it rains or even when there is little water leak, but the inventive concept has high reliability because a water leak range due to a water leak is measured. Also, since there is a need to bury only a transmission device, it is cheap, it is easy to install and it is possible to reduce an installation cost. Since it is also possible to detect the generation of a cavity when data is continuously observed, it is possible to prevent a disaster according to the generation of the cavity.

Although the detailed description of the inventive concept has provided particular embodiments, there may be many variations without departing from the scope of the inventive concept. Therefore, the scope of the inventive concept should not be limited to the above-described embodiments but should be defined by equivalents of the following claims as well as the following claims.

What is claimed is:

1. A medium change detection device comprising:
   an ultrasonic/wireless transmission device disposed under an underground target and configured to transmit an ultrasonic signal and a radio frequency (RF) signal toward a surface of earth; and
   at least one ultrasonic/wireless reception device disposed on a surface of earth over the underground target and configured to receive the ultrasonic signal and the RF signal transmitted from the ultrasonic/wireless transmission device,
   wherein the medium change detection device uses the RF signal as a triggering signal and measures an arrival time of the ultrasonic signal received by the ultrasonic/wireless reception device to detect a size of an underground soil component on a reception path of the ultrasonic signal based on a size of a sound speed that varies depending on a component of a medium on the reception path.

2. The medium change detection device of claim 1, wherein the ultrasonic/wireless reception device is disposed in plurality at constant intervals on the surface of the earth to 3-dimensionally detect the size of the underground soil component.

3. The medium change detection device of claim 2, wherein the ultrasonic signal is a signal of a pulse wave form or sine wave form, and measurement of the arrival time is obtained by using a difference between the pulses of the ultrasonic signal and the RF signal or a difference between phases.

4. The medium change detection device of claim 2, wherein the ultrasonic/wireless reception devices are disposed on a concentric circle in a radial direction or disposed in a polygon comprising a quadrilateral, such as a checker board.

5. The medium change detection device of claim 1, wherein an arrival time of an ultrasonic signal measured immediately after the ultrasonic/wireless transmission device and the ultrasonic/wireless reception device are installed is set as a criterion, and an arrival time of the ultrasonic signal measured after a certain time is compared with the set criterion to detect a change in medium between the underground target and the surface of the earth on a signal path.

6. The medium change detection device of claim 1, wherein by measuring a speed difference relative to a change in underground medium after calculating an ultrasonic speed in the medium between the underground target and the surface of the earth through mathematical modeling, a water leak, sinkhole (cavity) or pollution of the underground target is detected.

7. The medium change detection device of claim 1, wherein the RF signal increases or decreases in frequency according to an attenuation level on the surface of the earth, and is a signal of a pulse wave form or sine wave form.

8. The medium change detection device of claim 1, wherein the ultrasonic/wireless transmission device has a structure in which power is provided from a primary battery and thus there is no need for an external power supply, a structure in which power is received through a power cable extended from the surface of the earth, or a structure in which a secondary battery is included and charging is performed wirelessly through a magnetic field or ultrasonic wave provided from the surface of the earth.

9. The medium change detection device of claim 1, wherein the ultrasonic/wireless reception devices are capable of performing wired and wireless communication between reception devices and one of them is connected to an external communication network through a sensor gateway to be capable of obtaining operation and measurement data on a transmission and reception device remotely.

10. The medium change detection device of claim 1, wherein the ultrasonic/wireless reception device is configured to communicate with the ultrasonic/wireless transmission device wirelessly or by using an ultrasonic wave and remotely change the ultrasonic/wireless transmission device to a sleep mode or operating mode.

11. The medium change detection device of claim 10, wherein the ultrasonic/wireless reception device and the ultrasonic/wireless transmission device are configured to be automatically changed to the sleep mode when being in a non-operating mode for a certain time.

12. The medium change detection device of claim 11, wherein when there is one or more ultrasonic/wireless transmission devices, transmission times are different from each other to identify an ultrasonic signal transmitted from each transmission device or the number of name of each transmission device is identified by a header signal of the signal to transmit the ultrasonic signal.

13. The medium change detection device of claim 1, wherein the ultrasonic/wireless reception device is configured to communicate with the ultrasonic/wireless transmission device wirelessly or by using an ultrasonic wave, change the ultrasonic/wireless transmission device from a sleep mode to an operating mode to perform periodic measurement, and then remotely change the ultrasonic/wireless transmission device to the sleep mode.

14. The medium change detection device of claim 1, wherein when there is one or more ultrasonic/wireless transmission devices, there is also one or more ultrasonic/wireless reception devices and the ultrasonic/wireless transmission devices and the ultrasonic/wireless reception devices are combined each other to detect a change in medium in the underground target.

* * * * *